Figure 1:
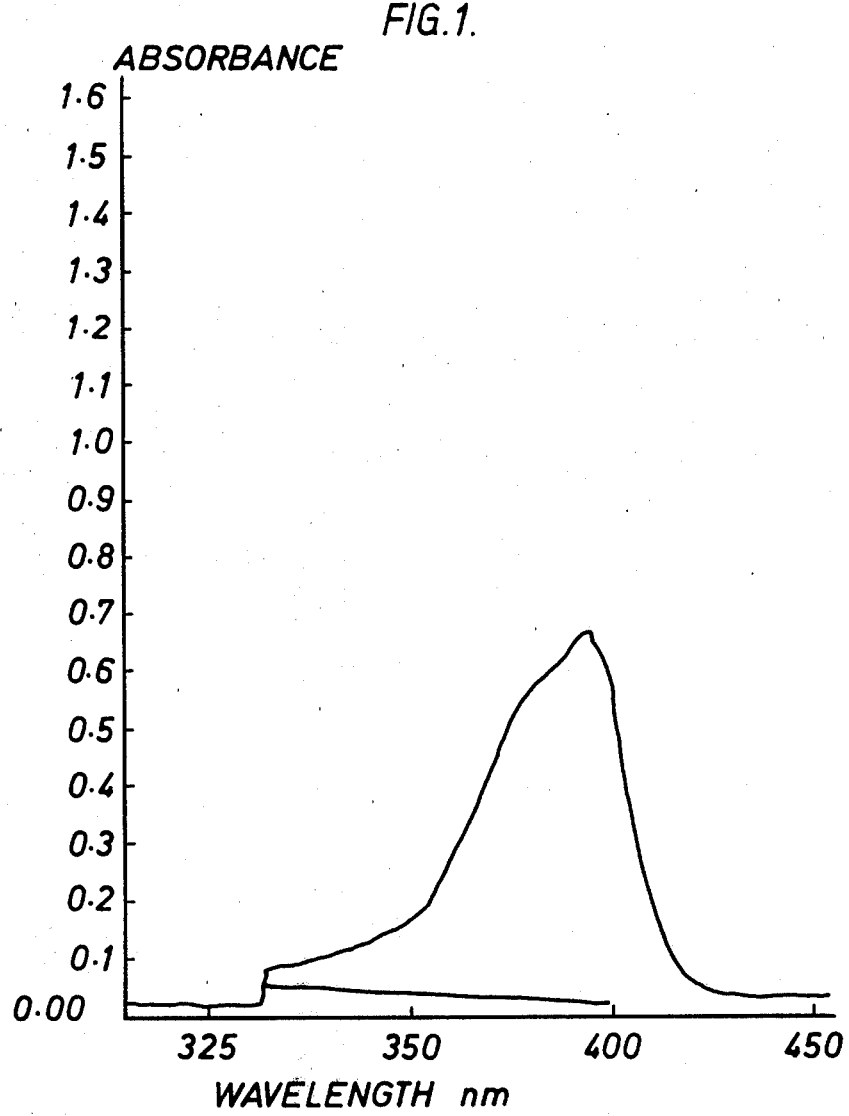
Figure 2:
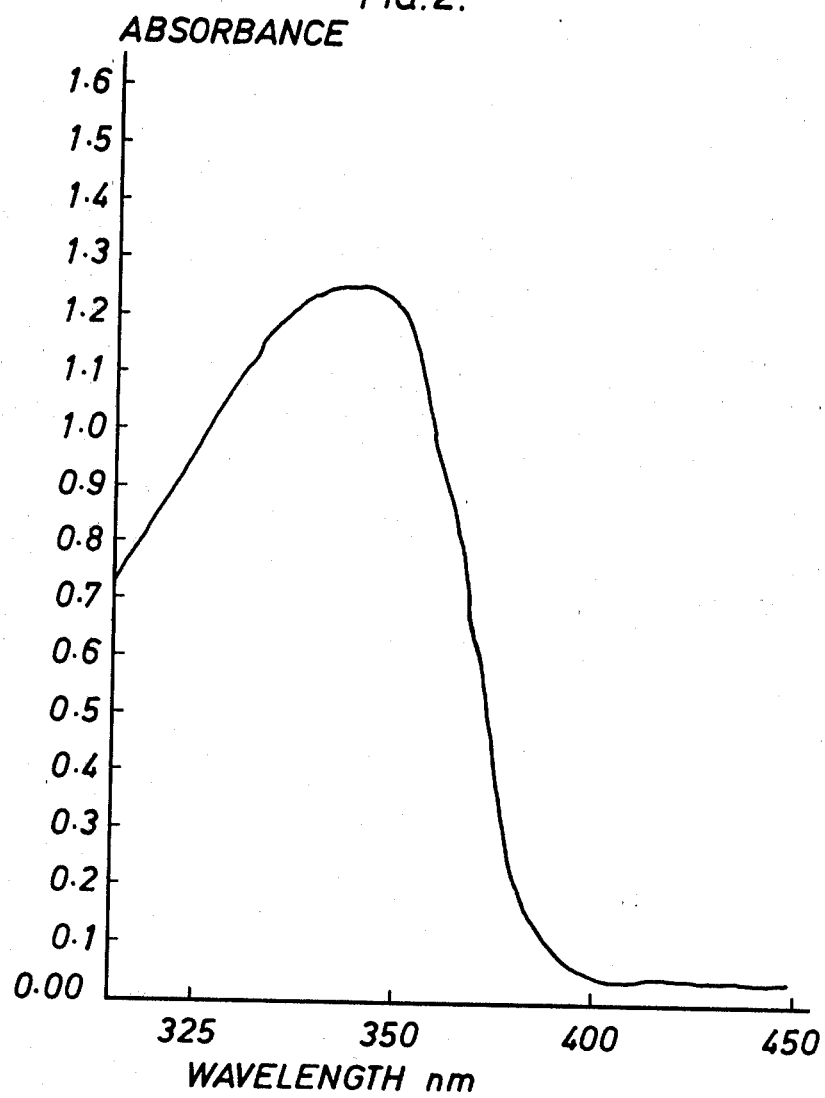
Figure 3:
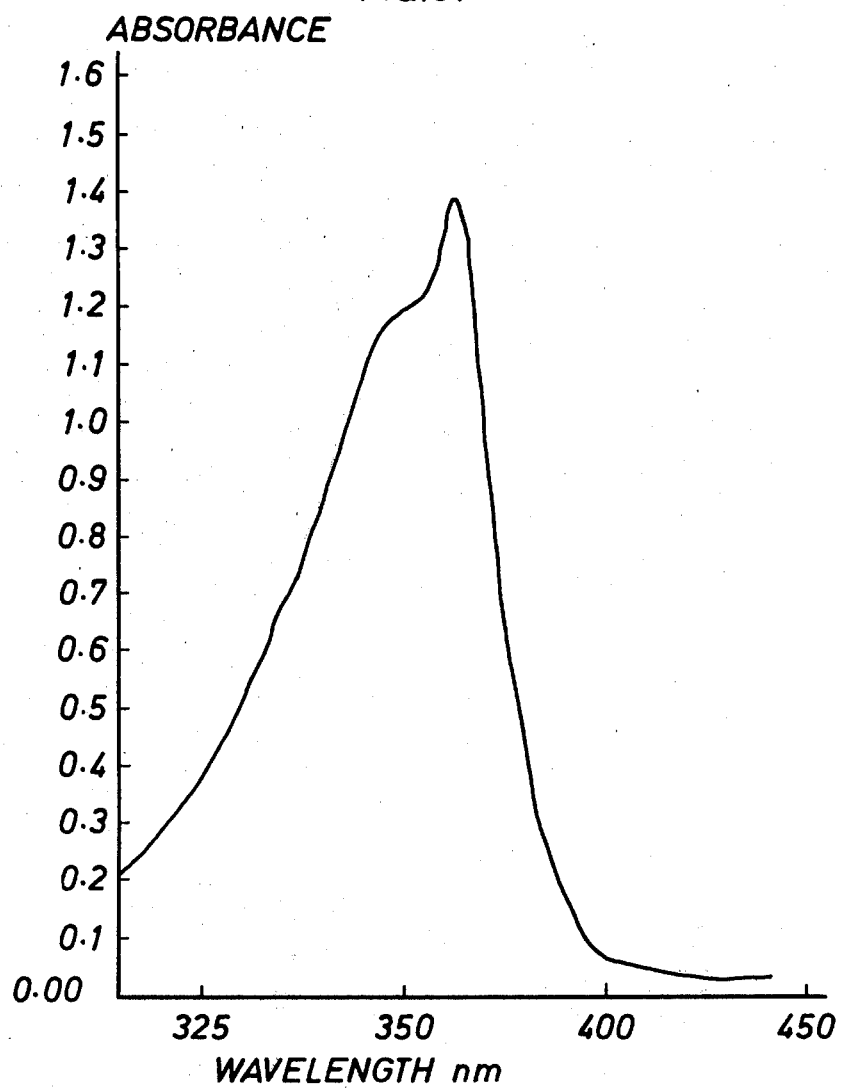

United States Patent [19]

Postle

[11] 4,360,588
[45] Nov. 23, 1982

[54] PHOTOGRAPHIC ELEMENT CONTAINING A UV-FILTER LAYER

[75] Inventor: Stephen R. Postle, Brentwood, England

[73] Assignee: Ciba-Geigy AG, Basle, Switzerland

[21] Appl. No.: 291,698

[22] Filed: Aug. 10, 1981

[30] Foreign Application Priority Data

Aug. 29, 1980 [GB] United Kingdom ............... 8028072

[51] Int. Cl.³ ............................................. G03C 1/78
[52] U.S. Cl. .................................... 430/512; 430/931; 523/135
[58] Field of Search ................... 430/512, 931, 4; 523/135; 350/1.1

[56] References Cited

U.S. PATENT DOCUMENTS 4,052,216 10/1977 Sobel et al. ........................ 430/931
4,245,018 1/1981 Hara et al. ........................ 430/512
4,309,500 1/1982 Shishido .......................... 430/515

Primary Examiner—Jack P. Brammer

Attorney, Agent, or Firm—Joseph G. Kolodny

[57] ABSTRACT

Light-sensitive photographic material which contains a non-light sensitive uv-filter layer comprising a compound of the formula

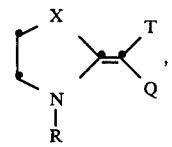

wherein R is alkyl, sulphoalkyl, carboxyalkyl, alkaryl or aryl, X is —S—, —$CH_2$— or —$C(CH_3)_2$—, T and Q are each an organic grouping or together complete a carbocyclic or heterocyclic ring, there being present in at least one of T and Q or in the ring which together they complete at least one electron withdrawing group.

These compounds exhibit a very sharp cut-off point at about 400 nm.

13 Claims, 3 Drawing Figures

PHOTOGRAPHIC ELEMENT CONTAINING A UV-FILTER LAYER

The present invention relates to light-sensitive photographic material which comprises an ultra-violet light (uv) absorbing layer.

It is common in photograpic materials and in particular in colour photographic materials to provide uv-absorbing layer to minimise the tendency of high-light areas which are not in fact blue from appearing blue in the final print. Various uv-absorbing compounds have been used for this purpose and their chief requirement is that they absorb all actinic light below 400 nm but have a very sharp cut-off point at about 400 nm. It has now been found that a class of known compounds can be used in uv-absorbing layers because they have such a sharp cut-off point.

According to the present invention there is provided a light-sensitive photographic material which contains a non-light sensitive uv-filter layer comprising a compound of the general formula

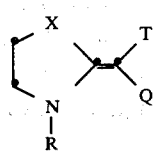 (1)

wherein R is alkyl, sulphoalkyl, carboxyalkyl, alkaryl or aryl, X is —S—, —CH$_2$— or —C(CH$_3$)$_2$—, T and Q are each an organic grouping or together complete a carbocyclic or heterocyclic ring, there being present in at least one of T or Q or in the ring which together they complete at least one electron withdrawing group selected from the group consisting of =C=O, —CN and —SO$_2$R′, wherein R′ is alkyl or aryl or —OR″, wherein R″ is alkyl or aryl or hydrogen or R′ is —NHR‴, wherein R‴ is hydrogen or alkyl or aryl.

Another object of the present invention is a process for the manufacture of the inventive material.

Suitable alkyl radicals of R are lower alkyl radicals such as methyl, ethyl, propyl, butyl or t-butyl. R denotes further sulphoalkyl or carboxyalkyl. In these groups, the alkyl moiety also contains 1 to 4 carbon atoms and those species are preferred which just have been mentioned. In the meaning of alkaryl, the aryl moiety is preferably a naphthyl or more preferable a phenyl ring. These ring systems are optionally substituted by alkyl having 1 to 4 carbon atoms, the radicals cited above being preferred. Alkyl having 1 to 4 carbon atoms, especially methyl, is the mostly preferred meaning of R.

X is —C(CH$_3$)$_2$— or, more preferred, —S— or —CH$_2$—.

T and Q are each an organic grouping. These organic groupings contain at least one electron withdrawing group such as a carbonyl, cyano, alkyl sulfone, aryl sulfone, sulfone amide, hydroxy, alkoxy or aryloxy group. The organic groupings can represent a carbocyclic species, substituted by at least one of those electron withdrawing groups and optically further substituted by alkyl having 1 to 4 carbon atoms. Preferably, these carbocyclic groupings are unsaturated. It is further possible that an electron withdrawing group, preferably the carbonyl group, which is substituted on such an organic grouping, provides the linkage to the group of the formula

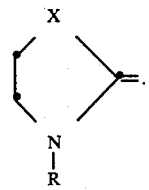 (2)

T and Q complete together a carbocyclic ring. This ring system, preferbly 5- or 6-membered, is saturated and optionally substituted by alkyl having 1 to 4 carbon atoms and at least by one of said electron withdrawing groups. Further, T and Q form together a heterocyclic ring, which is preferably 5-membered, saturated or unsaturated and substituted by at least one of said electron withdrawing groups and ballasting groups. Suitable ballasting groups are long chain alkyl groups having from 10 to 20 carbon atoms, such as decyl, dodecyl, hexadecyl, heptadecyl, octadecyl and eicosyl as well as isomers thereof. Further suitable ballasting groups are halogenated phenyl rings and phenyl amino groups, wherein the phenyl rings are further substituted by halogen, such as chlorine or bromine, and/or by an acylamino group. This acyl moiety contains at least 15 carbon atoms. Preferred heterocyclic ring systems formed by T together with Q are derived e.g. from thiohydantoine, rhodanine, oxarhodanine or pyrazolone radicals.

A suitable light-sensitive silver halide material contains a compound of the formula (1), wherein R is alkyl having 1 to 4 carbon atoms, sulphoalkyl or carboxyalkyl, wherein the alkyl moiety contains 1 to 4 carbon atoms, or R is phenyl.

More preferred is a material, wherein R in the compound of formula (1) is alkyl having 1 to 4 carbon atoms.

Interesting material contains a compound of the formula (1), wherein X is —S— or —CH$_2$—.

More suitable is a material, wherein in the compound of formula (1) T and Q together complete a thiohydantoine, rhodanine, oxarhodanine or pyrazolone ring.

There is high interest in a material, wherein T and Q in the compound of formula (1) together complete a rhodanine, an oxarhodanine or pyrazolone ring.

Preferably, a material is used, wherein T and Q in the compound of formula (1) complete a cyclohexanedion ring which is optionally substituted by alkyl having 1 to 4 carbon atoms.

Mostly preferred is a material, wherein T and Q in the compound of formula (1) are each benzoyl.

The most suitable material contains a compound of the formula (1), wherein R is alkyl having 1 to 4 carbon atoms, X is —S— or —CH$_2$—, and T and Q are each benzoyl or form together a cyclohexanedion, rhodanine, oxarhodanine or pyrazolone ring.

Preferably the photographic material comprises in the supercoat layer the compounds of formula (1). Most preferably the supercoat layer is a non-light sensitive gelatin layer and the compound of formula (1) have been added to the aqueous gelatin coating solution from which the supercoat is prepared either as an aqueous solution or as an organic solvent solution wherein the organic solvent is water-miscible. Alternatively the compounds of formula (1) may be present in the layer of the photographic material as an oil dispersion or as a solid dispersion.

The coating weight of the compounds of formula (1) in the uv-filter layer is usually within the range of 1–10 mg/dm$^2$.

The compounds of formula (1) when formulated in a uv-filter layer absorb all uv-light up to and including 400 nm light but their absorption does not extend appreciably into visible region of the spectrum. Thus the compounds are either colourless or very pale yellow. They have no appreciable visible density at the coating weight usually employed for filter layers.

The compounds of formula (1) are dyes of the class known as merocyanines. Merocyanine dyes can act as optical sensitizers for silver halide and other light-sensitive compositions and thus in the material of the present invention it is important that the compounds of formula (1) are not present in the same layer as the silver halide or other light-sensitive compositions. Most of the compounds covered by formula (1) are poor optical sensitizers but if they are present in the same layer as the light-sensitive composition they could displace other optical sensitizers already present and thus reduce or alter the optical sensitization of the composition.

The compounds of formula (1) may be prepared by many well known routes, for example the routes described in "The Chemistry of Synthetic Dyes", K. Venkataraman, Academic Press, N.Y. 1971.

The following preparations will serve to illustrate the preparations of three compounds of formula (1).

PREPARATION 1

3-Methyl-2-thiomethyl thiazolidinium iodide (2.75 g, $10^{-2}$ mol) and 3octadecylrhodanine (3.85 g, $10^{-2}$ mol) are heated under reflux for 20 minutes with triethylamine (1.01 g) and ethanol (10 ml). The mixture is cooled and the white solid filtered, washed with ethanol and recrystallised from ethanol (3.15 g). The dye has the formula

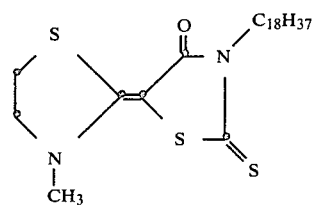
(100)

Figure I shows the uv-spectrum, measured in methanol solution. It is substantially similar in oil emulsion coated in gelatine on clear base ($\lambda$ max 394 nm; $\epsilon$ max 3.1 $\times 10^4$).

PREPARATION 2

1-Methyl-2-thiomethyl pyrrolidinium tosylate (2.65 g, 8.75$\times 10^3$ mol) and dibenzoyl methane (1.96 g, 8.75$\times 10^{-3}$ mol) are heated under reflux in ethanol (10 ml) with triethylamine (1 ml). The reaction mixture is evaporated to small volume and the oil covered with ether. Crystals are deposited after 5 days. These are washed with ethanol and recrystallised from ethanol (0.91 g). The dye has the formula

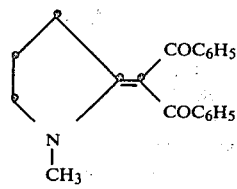
(101)

Figure II shows the acetone solution spectrum of this compound ($\lambda$max 340 nm; $\epsilon$max 3.7$\times 10^4$), which is essentially unaltered in oil emulsions coated in gelatin on clear base.

PREPARATION 3

1-Methyl-2-thiomethyl pyrrolidinium tosylate (3.01 g, $10^{-2}$ mol) and 3-dodecyl thiohydantoin (2.68 g, $10^{-2}$ mol) are heated under reflux in ethanol (10 ml) with triethylamine (1.01 g) for 20 minutes. The reaction mixture is evaporated to small volume and cooled, and scratched under ethanol (1 ml) furnishing crystals. These are recrystallised from ethanol (1.85 g). The dye has the formula

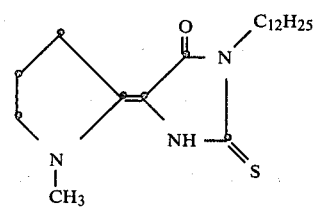
(102)

A uv-spectrum, measured in methanol, which is substantially the same as that of an oil dispersion in gelatin coated on clear base, is shown in Figure III ($\lambda$ max 373 nm; $\epsilon$ max 4.84$\times 10^4$).

Other useful compounds are the following:

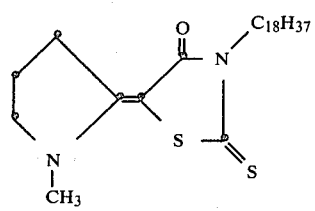
(103)

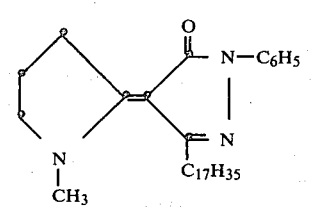
(104)

-continued (105)

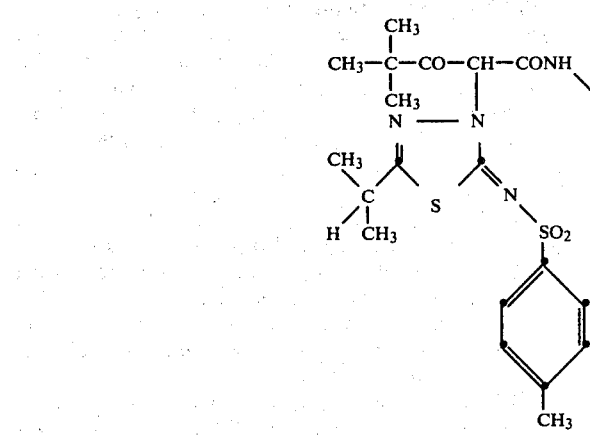

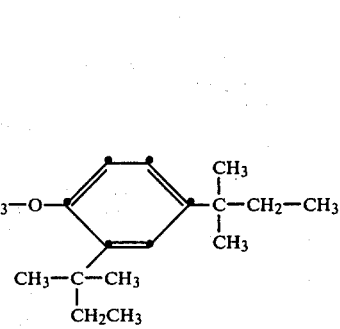

dispersed in it 30 mg of the yellow colour coupler of formula (108)

5-γ{-[2,4-Bis(1,1-dimethylpropyl)phenoxy]-butyramido}-2-chloro-α-[5-isopropyl-2-(4-tolylsulphonylimino)-Δ⁴-1,3,4-thiadiazolin-3-yl]-α-pivaloylacetanilide in tri-isopropyl phenyl phosphate. The resulting emulsion is coated on to 1 dm² of subbed polyester support and the coating dried.

On this silver halide emulsion layer there is coated a non-stress layer which comprises compound (100) as a uv absorber. This layer is prepared as follows.

The following solution is prepared:

| | |
|---|---|
| Compound (100) | 1 g |
| Di-n-butyl phthalate (DBP) | 1 g |
| Ethyl acetate | 1 g |
| 10% gelatin solution | 8 g |
| 10% anionic wetting agent | 2 ml |
| Distilled water | 2 ml | by dissolving compound (100) in the DBP and ethyl acetate on a hot plate. Then the gelatin solution to which the distilled water and wetting agent has been added is heated to 50° C. The solution of compound (100) is added to the gelatin solution and mixed in an ultrasonic mixer for two minutes.

A gelatin non-stress layer is prepared containing

| | |
|---|---|
| Gelatin | 0.9 g |
| Distilled water | 22.5 g |
| Dispersion of compound (100) as just prepared | 1.75 g |
| 10% wetting agent | 0.7 ml |

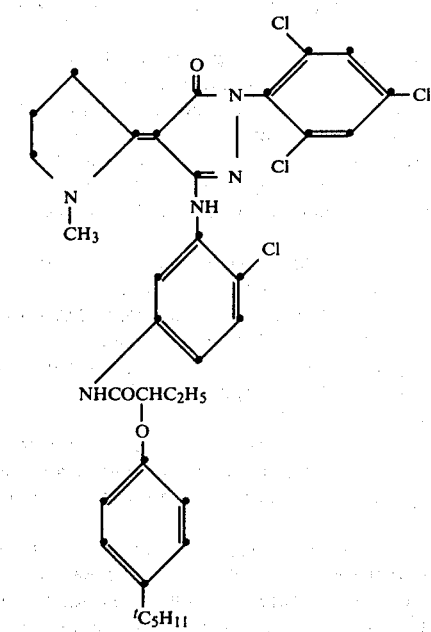

(106)

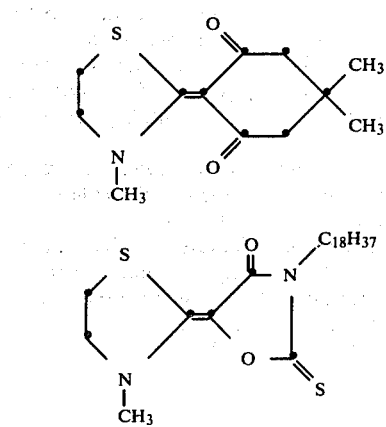

(107)

0.62 ml of this solution is coated on to the 1 dm² polyester support coated with the silver halide emulsion layer and the coating dried. The gelatin coating weight of the dried non-stress layer is 23.8 mg per 1 dm² and the coating weight of compound (100) is 2.8 mg per 1 dm².

A strip of this material (strip A) is taken and exposed with a standard step wedge to a tungsten halogen light source, and processed at 37.8° C. in the following solutions:

EXAMPLE

A photographic silver halide material having a uv-absorbing layer is prepared as follows:

A silver iodobromide emulsion containing 2% iodide to 98% bromide is prepared. A portion of this emulsion which contained 70 mg gelatine and 70 mg silver has

| | | |
|---|---|---|
| 1. Colour developing developer bath: | 3¼ | minutes |
| Potassium carbonate | 37.5 | g |
| Sodium metabisulphite (anhydrous) | 4.25 | g |

| | | |
|---|---|---|
| Potassium iodide | 2.0 | mg |
| Sodium bromide | 1.3 | g |
| Hydroxylamine sulphate | 2.0 | g |
| 4-(N—ethyl-N—β-hydroxyethylamino)-2-methylaniline sulphate | 4.75 | g |
| Water to make up to | 1 | liter. |
| 2. Bleaching | 6½ | minutes |
| bleaching bath: | | |
| Ammonium bromide | 150 | g |
| Ammonium salt of the iron-III-complex of ethylenediamine tetra-acetic acid | 175 | ml |
| Acetic acid (glacial acetic acid) | 10.5 | ml |
| Sodium nitrate | 35 | g |
| Water to make up to | 1 | liter. |
| 3. Washing | 3¼ | minutes |
| 4. Fixing | 6½ | minutes |
| fixing bath: | | |
| Ammonium thiosulphate (50% aqueous) | 16.2 | ml |
| Diethylenetriaminepenta-acetic acid | 1.25 | g |
| Sodium metabisulphite (anhydrous) | 12.4 | g |
| Sodium hydroxide | 2.4 | g |
| Water to make up to | 1 | liter. |
| 5. Washing | 3½ | minutes |
| 6. Stabilising | | |
| stabiliser bath: | | |
| Formaldehyde (35% aqueous solution) | 5.0 | ml |
| Water to make up to | 1 | liter. |

A yellow image is obtained showing that the film is sensitive to blue light. Another strip (A) is exposed briefly to a mercury vapour lamp, with a standard step wedge. After processing as above no image is obtained.

This shows that compound (100) acts as a uv-absorber during the exposure of the photographic material but is also present in the processed photographic material and thus would help to preserve the yellow dye image from deterioration caused by uv-light if the processed strip is to be used as a negative in subsequent exposing and printing operations.

A strip of material is then taken by coating the silver halide emulsion layer alone, without the uv-filter layer (strip B). Separate pieces of this are exposed to both the tungsten halogen light source and to the mercury vapour lamp. In each case an image is obtained after processing. This further demonstrates the uv absorbing nature of the compounds of this invention.

I claim:

1. A light-sensitive photographic element which contains a silver halide emulsion layer non-light sensitive uv-filter layer comprising a compound of the general formula

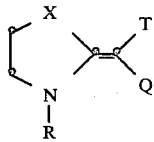
(1)

wherein R is alkyl, sulphoalkyl, carboxyalkyl, alkaryl or aryl, X is —S—, —CH$_2$— or —C(CH$_3$)$_2$—, T and Q are each an organic grouping or together complete a carbocyclic or heterocyclic ring, there being present in at least one of T or Q or in the ring which together they complete at least one electron withdrawing group selected from the group consisting of =C=O, —CN and —SO$_2$R', wherein R' is alkyl or aryl or —OR'', wherein R'' is alkyl or aryl or hydrogen or R' is —NHR''', wherein R''' is hydrogen or alkyl or aryl.

2. A light-sensitive element according to claim 1, wherein R is alkyl having 1 to 4 carbon atoms, sulphoalkyl or carboxyalkyl, wherein the alkyl moiety contains 1 to 4 carbon atoms, or R is phenyl.

3. Light-sensitive element according to claim 1 wherein R in the compound of formula (1) is alkyl having 1 to 4 carbon atoms.

4. Light-sensitive element according to claim 1 wherein X in the compound of formula (1) is —S— or —CH$_2$—.

5. Light-sensitive element according to claim 1, wherein in the compound of formula (1) T and Q together complete a thiohydantoine, rhodanine, oxarhodanine or pyrazolone ring.

6. Light-sensitive element according to claim 5, wherein T and Q in the compound of formula (1) together complete a rhodanine, an oxarhodanine or pyrazolone ring.

7. Light-sensitive element according to claim 1, wherein T and Q in the compound of formula (1) complete a cyclo-hexanedion ring which is optionally substituted by alkyl having 1 to 4 carbon atoms.

8. Light-sensitive element according to claim 1, wherein T and Q in the compound of formula (1) are each benzoyl.

9. Light-sensitive photographic element acording to claim 1, which is silver halide photosensitive material and the compound of formula (1) is present in a supercoat layer.

10. Light-sensitive photograpic element according to claim 9, wherein the supercoat layer is a gelatin layer and the compound of formula (1) has been added to an aqueous gelatin supercoat coating solution either as aqueous solution or as an organic solvent solution wherein the organic solvent is water-miscible.

11. Light-sensitive photographic element according to claim 9, wherein the compound of formula (1) is present in the supercoat layer as an oil dispersion or as a solid dispersion.

12. Light-sensitive photographic element according to claim 1, wherein the compound of formula (1) is present within the range of 1–10 mg/dm$^2$.

13. A process for the manufacture of a light-sensitive photographic element according to claim 1, wherein a compound of the formula (1) is incorporated into a non-light sensitive layer of the element.

* * * * *